US012760263B2

(12) United States Patent
Blanchard et al.

(10) Patent No.: US 12,760,263 B2
(45) Date of Patent: Oct. 13, 2026

(54) METHOD AND APPARATUS FOR PREVENTING CELL CULTURE PLATE CONDENSATION IN AN IMAGING SYSTEM

(71) Applicant: THRIVE BIOSCIENCE, INC., Wakefield, MA (US)

(72) Inventors: Alan Blanchard, Wakefield, MA (US); Jeff Goldman, Wakefield, MA (US)

(73) Assignee: THRIVE BIOSCIENCE, INC., Wakefield, MA (US)

( * ) Notice: Subject to any disclaimer, the term of this patent is extended or adjusted under 35 U.S.C. 154(b) by 633 days.

(21) Appl. No.: 18/267,683

(22) PCT Filed: Dec. 15, 2021

(86) PCT No.: PCT/US2021/063577
§ 371 (c)(1),
(2) Date: Jun. 15, 2023

(87) PCT Pub. No.: WO2022/132946
PCT Pub. Date: Jun. 23, 2022

(65) Prior Publication Data

US 2024/0101949 A1 Mar. 28, 2024

Related U.S. Application Data

(60) Provisional application No. 63/126,088, filed on Dec. 16, 2020.

(51) Int. Cl.
*C12M 1/00* (2006.01)
*B01L 7/00* (2006.01)
(Continued)

(52) U.S. Cl.
CPC ............... *C12M 41/12* (2013.01); *B01L 7/00* (2013.01); *C12M 25/06* (2013.01); *C12M 41/36* (2013.01); *B01L 2300/1827* (2013.01)

(58) Field of Classification Search
None
See application file for complete search history.

(56) References Cited

U.S. PATENT DOCUMENTS 9,180,461 B2 11/2015 Edens et al.
9,366,686 B2 6/2016 Stiles et al.
(Continued)

FOREIGN PATENT DOCUMENTS

GB 2539275 A 12/2016
WO 94/12405 A2 6/1994
(Continued)

OTHER PUBLICATIONS

International Search Report dated Feb. 3, 2022, in connection with PCT International Application No. PCT/US21/63577.
(Continued)

*Primary Examiner* — Jyoti Mutreja
(74) *Attorney, Agent, or Firm* — Norris McLaughlin, PA

(57) ABSTRACT

A method and apparatus for preventing condensation on a cell culture plate transferred from an incubator to an imager. A block having a higher thermal conductivity layer and a lower thermal conductivity layer is preheated in an incubator. The block is placed on a cell culture plate either before or immediately after removing the cell culture plate from an incubator with the higher thermal conductivity layer resting on the plate and configured to overlie all of the wells of the plate. The culture plate is transported to an imager with the thermal block in place and the block is removed before inserting the culture plate into the imager.

10 Claims, 8 Drawing Sheets

(51) Int. Cl.
*C12M 1/12* (2006.01)
*C12M 1/34* (2006.01)

(56) References Cited

U.S. PATENT DOCUMENTS

| | | | | |
|---|---|---|---|---|
| 11,319,523 | B2 * | 5/2022 | Blanchard .............. | C12M 41/14 |
| 2003/0147779 | A1 | 8/2003 | Azarani et al. | |
| 2020/0319217 | A1 | 10/2020 | Verhoef et al. | |

FOREIGN PATENT DOCUMENTS

| | | | |
|---|---|---|---|
| WO | 02/20161 | A1 | 3/2002 |
| WO | WO2018102781 | * | 6/2018 |

OTHER PUBLICATIONS

Written Opinion dated Mar. 21, 2022, in connection with PCT International Application No. PCT/US21/63577.

* cited by examiner

METHOD AND APPARATUS FOR PREVENTING CELL CULTURE PLATE CONDENSATION IN AN IMAGING SYSTEM

PRIORITY CLAIM

This application is a 371 of International Patent Application No. PCT/US2021/063577, filed Dec. 15, 2021, which claims priority of U.S. Provisional Application Ser. No. 63/126,088, filed Dec. 16, 2020, the disclosures of which patent applications are hereby incorporated herein by reference.

FIELD OF THE INVENTION

The present invention relates to imaging systems and in particular to imaging systems for cell cultures.

BACKGROUND

Cell culture incubators are used to grow and maintain cells from cell culture, which is the process by which cells are grown under controlled conditions. Cell culture vessels containing cells are stored within the incubator, which maintains conditions such as temperature and gas mixture that are suitable for cell growth. Cell imagers take images of individual or groups of cells for cell analysis.

Cell culture is a useful technique in both research and clinical contexts. However, maintenance of cell cultures, for example, long term cultures, tissue preparations, in vitro fertilization preparations, etc., in presently available cell incubators is a laborious process requiring highly trained personnel and stringent aseptic conditions.

While scientists use microscopes to observe cells during culturing and may also attach a camera to the microscope to image cells in a cell culture, such imaging systems have many disadvantages.

Condensation buildup is a common problem encountered when imaging live cells, especially when moving the tissue culture plate from an incubator to a dry, cool area. Upon removal from the incubator, the temperature gradient between the base and the lid rapidly increases, with the lid cooling much faster than the media-containing base. This causes condensation to quickly build up on the lid.

SUMMARY

The object of the present invention is to provide an improved imaging system and method for cells in a cell culture. An imaging system and method of this type is described in U.S. application Ser. No. 15/563,375 filed on Mar. 31, 2016 and the disclosure of which in its entirety is hereby incorporated by reference.

Another object of the invention is to prevent the buildup of condensation when a plate is moved from an incubator into an imager. Methods and apparatuses for obtaining this object are disclosed.

In some embodiments, the imaging system and method described herein can be used as a stand-alone imaging system or it can be integrated in a cell incubator using a transport described in the aforementioned application incorporated by reference. In some embodiments, the imaging system and method is integrated in a cell incubator and includes a transport.

In some embodiments the system and method acquire data and images at the times a cell culturist typically examines cells. The method and system provide objective data, images, guidance and documentation that improves cell culture process monitoring and decision-making.

The system and method in some embodiments enable sharing of best practices across labs, assured repeatability of process across operators and sites, traceability of process and quality control. In some embodiments the method and system provide quantitative measures of cell doubling rates, documentation and recording of cell morphology, distribution and heterogeneity.

In some embodiments, the method and system provide assurance that cell lines are treated consistently and that conditions and outcomes are tracked. In some embodiments the method and system learn through observation and records how different cells grow under controlled conditions in an onboard database. Leveraging this database of observations, researchers are able to profile cell growth, test predictions and hypotheses concerning cell conditions, media and other factors affecting cell metabolism, and determine whether cells are behaving consistently and/or changing.

In some embodiments the method and system enable routine and accurate confluence measurements and imaging and enables biologists to quantify responses to stimulus or intervention, such as the administration of a therapeutic to a cell line.

The method and system capture the entire well area with higher coverage than conventional images and enables the highest level of statistical rigor for quantifying cell status and distribution.

In some embodiments, the method and system provide image processing and algorithms that will deliver an integration of individual and group morphologies with process-flow information and biological outcomes. Full well imaging allows the analysis and modeling of features of groups of cells—conducive to modeling organizational structures in biological development. These capabilities can be used for prediction of the organizational tendency of culture in advance of functional testing.

In some embodiments, algorithms are used to separate organizational patterns between samples using frequency of local slope field inversions. Using some algorithms, the method and system can statistically distinguish key observed differences between iP-MSCs generated from different TCP conditions. Biologically, this work could validate serum-free differentiation methods for iPSC MSC differentiation. Computationally, the method and system can inform image-processing of MSCs in ways that less neatly "clustered" image sets are not as qualified to do.

Even if all iP-MSC conditions have a sub-population of cells that meets ISCT 7-marker criteria, the "true MSC" sub-populations may occupy a different proportion under different conditions or fate differences could be implied by tissue "meso-structures". By starting with a rich pallet of MSC outcomes, and grounding them in comparative biological truth, the method and system can refine characterization perspectives around this complex cell type and improve MSC bioprocess.

In certain embodiments, an imager includes one or more lenses, fibers, cameras (e.g., a charge-coupled device camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments the imager is a phase-contrast microscope. In other embodiments, the imager is a fluorescence imager or microscope.

As used herein, the fluorescence imager is an imager which is able to detect light emitted from fluorescent markers present either within or on the surface of cells or other biological entities, said markers emitting light in a specific wavelength when absorbing a light of different specific excitation wavelength.

As used herein, a "bright-field microscope" is an imager that illuminates a sample and produces an image based on the light absorbed by the sample. Any appropriate bright-field microscope may be used in combination with an incubator provided herein.

As used herein, a "phase-contrast microscope" is an imager that converts phase shifts in light passing through a transparent specimen to brightness changes in the image. Phase shifts themselves are invisible but become visible when shown as brightness variations. Any appropriate phase-contrast microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

Holographic Microscopy

In some embodiments, holographic microscopy is used to obtain images (e.g., a collection of three-dimensional microscopic images) of cells for analysis (e.g., cell counting) during culture (e.g., long-term culture) in an incubator (e.g., within an internal chamber of an incubator as described herein). In some embodiments, a holographic image is created by using a light field, from a light source scattered off objects, which is recorded and reconstructed. In some embodiments, the reconstructed image can be analyzed for a myriad of features relating to the objects. In some embodiments, methods provided herein involve holographic interferometric metrology techniques that allow for non-invasive, marker-free, quick, full-field analysis of cells, generating a high resolution, multi-focus, three-dimensional representation of living cells in real time.

In some embodiments, holography involves shining a coherent light beam through a beam splitter, which divides the light into two equal beams: a reference beam and an illumination beam. In some embodiments, the reference beam, often with the use of a mirror, is redirected to shine directly into the recording device without contacting the object to be viewed. In some embodiments, the illumination beam is also directed, using mirrors, so that it illuminates the object, causing the light to scatter. In some embodiments, some of the scattered light is then reflected onto the recording device. In some embodiments, a laser is generally used as the light source because it has a fixed wavelength and can be precisely controlled. In some embodiments, to obtain clear images, holographic microscopy is often conducted in the dark or in low light of a different wavelength than that of the laser in order to prevent any interference. In some embodiments, the two beams reach the recording device, where they intersect and interfere with one another. In some embodiments, the interference pattern is recorded and is later used to reconstruct the original image. In some embodiments, the resulting image can be examined from a range of different angles, as if it was still present, allowing for greater analysis and information attainment.

In some embodiments, digital holographic microscopy is used in incubators described herein. In some embodiments, digital holographic microscopy light wave front information from an object is digitally recorded as a hologram, which is then analyzed by a computer with a numerical reconstruction algorithm. In some embodiments, the computer algorithm replaces an image forming lens of traditional microscopy. The object wave front is created by the object's illumination by the object beam. In some embodiments, a microscope objective collects the object wave front, where the two wave fronts interfere with one another, creating the hologram. Then, the digitally recorded hologram is transferred via an interface (e.g., IEEE1394, Ethernet, serial) to a PC-based numerical reconstruction algorithm, which results in a viewable image of the object in any plane.

In some embodiments, in order to procure digital holographic microscopic images, specific materials are utilized. In some embodiments, an illumination source, generally a laser, is used as described herein. In some embodiments, a Michelson interferometer is used for reflective objects. In some embodiments, a Mach-Zehnder interferometer for transmissive objects is used. In some embodiments, interferometers can include different apertures, attenuators, and polarization optics in order to control the reference and object intensity ratio. In some embodiments, an image is then captured by a digital camera, which digitizes the holographic interference pattern. In some embodiments, pixel size is an important parameter to manage because pixel size influences image resolution. In some embodiments, an interference pattern is digitized by a camera and then sent to a computer as a two-dimensional array of integers with 8-bit or higher grayscale resolution. In some embodiments, a computer's reconstruction algorithm then computes the holographic images, in addition to pre- and post-processing of the images.

Phase Shift Image

In some embodiments, in addition to the bright field image generated, a phase shift image results. Phase shift images, which are topographical images of an object, include information about optical distances. In some embodiments, the phase shift image provides information about transparent objects, such as living biological cells, without distorting the bright field image. In some embodiments, digital holographic microscopy allows for both bright field and phase contrast images to be generated without distortion. Also, both visualization and quantification of transparent objects without labeling is possible with digital holographic microscopy. In some embodiments, the phase shift images from digital holographic microscopy can be segmented and analyzed by image analysis software using mathematical morphology, whereas traditional phase contrast or bright field images of living unstained biological cells often cannot be effectively analyzed by image analysis software.

In some embodiments, a hologram includes all of the information pertinent to calculating a complete image stack. In some embodiments, since the object wave front is recorded from a variety of angles, the optical characteristics of the object can be characterized, and tomography images of the object can be rendered. From the complete image stack, a passive autofocus method can be used to select the focal plane, allowing for the rapid scanning and imaging of surfaces without any vertical mechanical movement. Furthermore, a completely focused image of the object can be created by stitching the sub-images together from different focal planes. In some embodiments, a digital reconstruction algorithm corrects any optical aberrations that may appear in traditional microscopy due to image-forming lenses. In some embodiments, digital holographic microscopy advantageously does not require a complex set of lenses; but rather, only inexpensive optics, and semiconductor components are used in order to obtain a well-focused image, making it relatively lower cost than traditional microscopy tools.

Applications

In some embodiments, holographic microscopy can be used to analyze multiple parameters simultaneously in cells, particularly living cells. In some embodiments, holographic microscopy can be used to analyze living cells, (e.g., responses to stimulated morphological changes associated with drug, electrical, or thermal stimulation), to sort cells, and to monitor cell health. In some embodiments, digital holographic microscopy counts cells and measures cell viability directly from cell culture plates without cell labeling. In other embodiments, the imager can be used to examine apoptosis in different cell types, as the refractive index changes associated with the apoptotic process can be quantified via digital holographic microscopy. In some embodiments, digital holographic microscopy is used in research regarding the cell cycle and phase changes. In some embodiments, dry cell mass (which can correlate with the phase shift induced by cells), in addition to other non-limiting measured parameters (e.g., cell volume, and the refractive index), can be used to provide more information about the cell cycle at key points.

In some embodiments, the method is also used to examine the morphology of different cells without labeling or staining. In some embodiments, digital holographic microscopy can be used to examine the cell differentiation process; providing information to distinguish between various types of stem cells due to their differing morphological characteristics. In some embodiments, because digital holographic microscopy does not require labeling, different processes in real time can be examined (e.g., changes in nerve cells due to cellular imbalances). In some embodiments, cell volume and concentration may be quantified, for example, through the use of digital holographic microscopy's absorption and phase shift images. In some embodiments, phase shift images may be used to provide an unstained cell count. In some embodiments, cells in suspension may be counted, monitored, and analyzed using holographic microscopy.

In some embodiments, the time interval between image acquisitions is influenced by the performance of the image recording sensor. In some embodiments, digital holographic microscopy is used in time-lapse analyses of living cells. For example, the analysis of shape variations between cells in suspension can be monitored using digital holographic images to compensate for defocus effects resulting from movement in suspension. In some embodiments, obtaining images directly before and after contact with a surface allows for a clear visual of cell shape. In some embodiments, a cell's thickness before and after an event can be determined through several calculations involving the phase contrast images and the cell's integral refractive index. Phase contrast relies on different parts of the image having different refractive index, causing the light to traverse different areas of the sample with different delays. In some embodiments, such as phase contrast microscopy, the out of phase component of the light effectively darkens and brightens particular areas and increases the contrast of the cell with respect to the background. In some embodiments, cell division and migration are examined through time-lapse images from digital holographic microscopy. In some embodiments, cell death or apoptosis may be examined through still or time-lapse images from digital holographic microscopy.

In some embodiments, digital holographic microscopy can be used for tomography, including but not limited to, the study of subcellular motion, including in living tissues, without labeling.

In some embodiments, digital holographic microscopy does not involve labeling and allows researchers to attain rapid phase shift images, allowing researchers to study the minute and transient properties of cells, especially with respect to cell cycle changes and the effects of pharmacological agents.

Condensation buildup is a common problem encountered when imaging live cells, especially when moving the tissue culture plate from an incubator to a dry, cool area. Upon removal from the incubator, the temperature gradient between the base and the lid rapidly increases, with the lid cooling much faster than the media-containing base. This causes condensation to quickly build up on the lid.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

DETAILED DESCRIPTION

Figure 1:
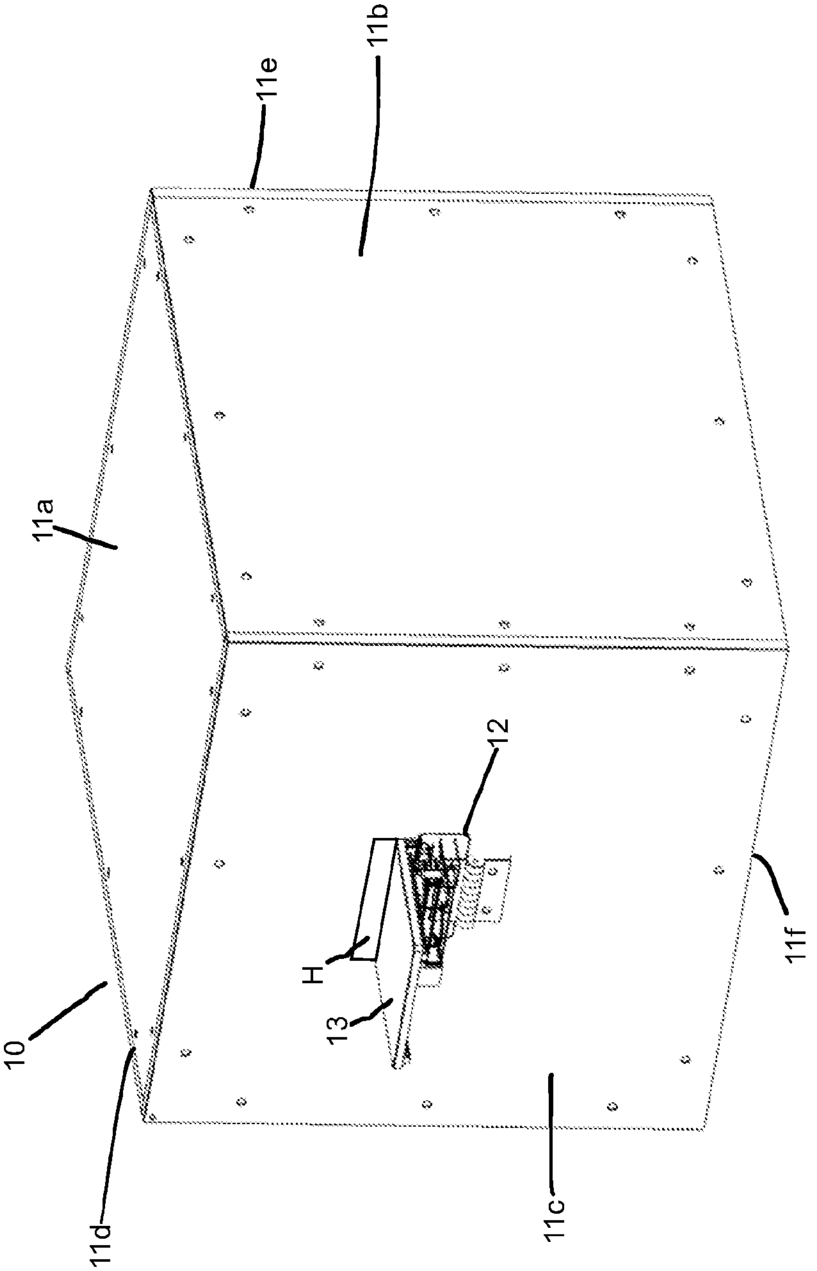
FIG. 1 is a perspective view of the imaging system according to the invention.

Referring now to FIG. 1, a cell imaging system 10 is shown. Preferably, the system 10 is fully encased with walls 11*a*-11*f* so that the interior of the imager can be set at 98.6 degrees F. with a $CO_2$ content of 5%, so that the cells can remain in the imager without damage. The temperature and the $CO_2$ content of the air in the system 10 is maintained by a gas feed port 14 (shown in FIG. 2) in the rear wall 11*e*.

Alternatively, a heating unit can be installed in the system 10 to maintain the proper temperature.

At the front wall 11*c* of the system 10, is a door 12 that is hinged to the wall 11*c* and which opens a hole H through which the sliding platform 13 exits to receive a plate and closes hole H when the platform 13 is retracted into the system 10.

The system 10 can also be connected to a computer or tablet for data input and output and for the control of the system. The connection is by way of an ethernet connector 15 in the rear wall 11*e* of the system as shown in FIG. 2.

Figure 2:
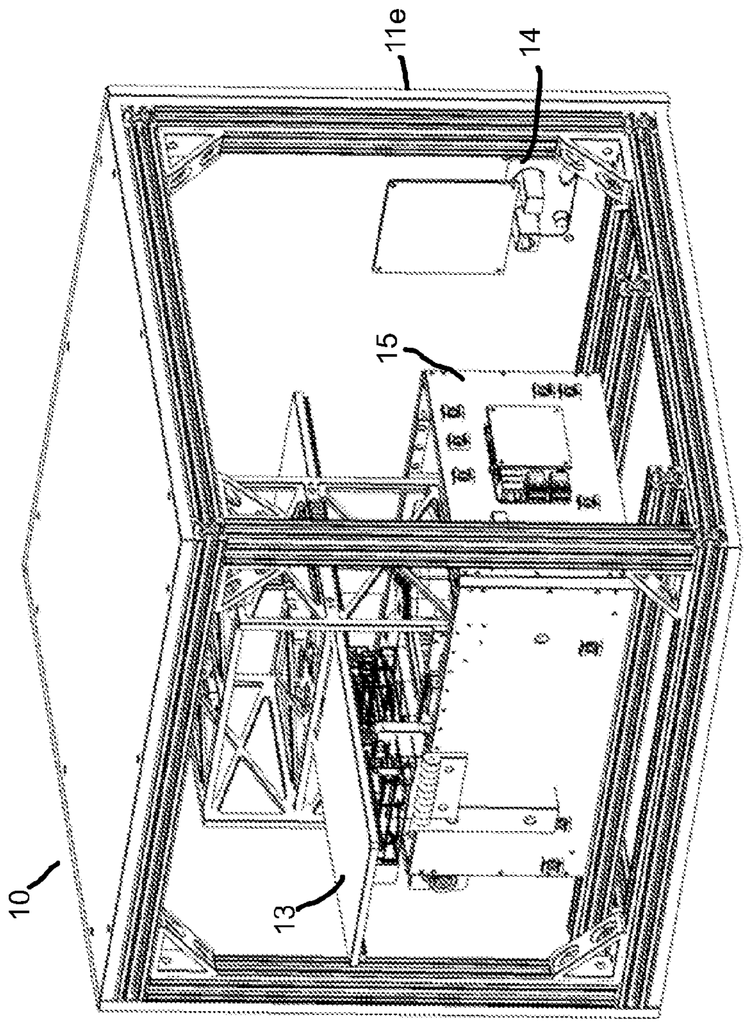
FIG. 2 is the imaging system of FIG. 1 with walls removed to reveal the internal structure.

FIG. 2 shows the system with walls 11*b* and 11*c* removed to show the internal structure. The extent of the platform 13 is shown as well as the circuit board 15 that contains much of the circuitry for the system, as will be explained in more detail hereinafter.

Figure 3:
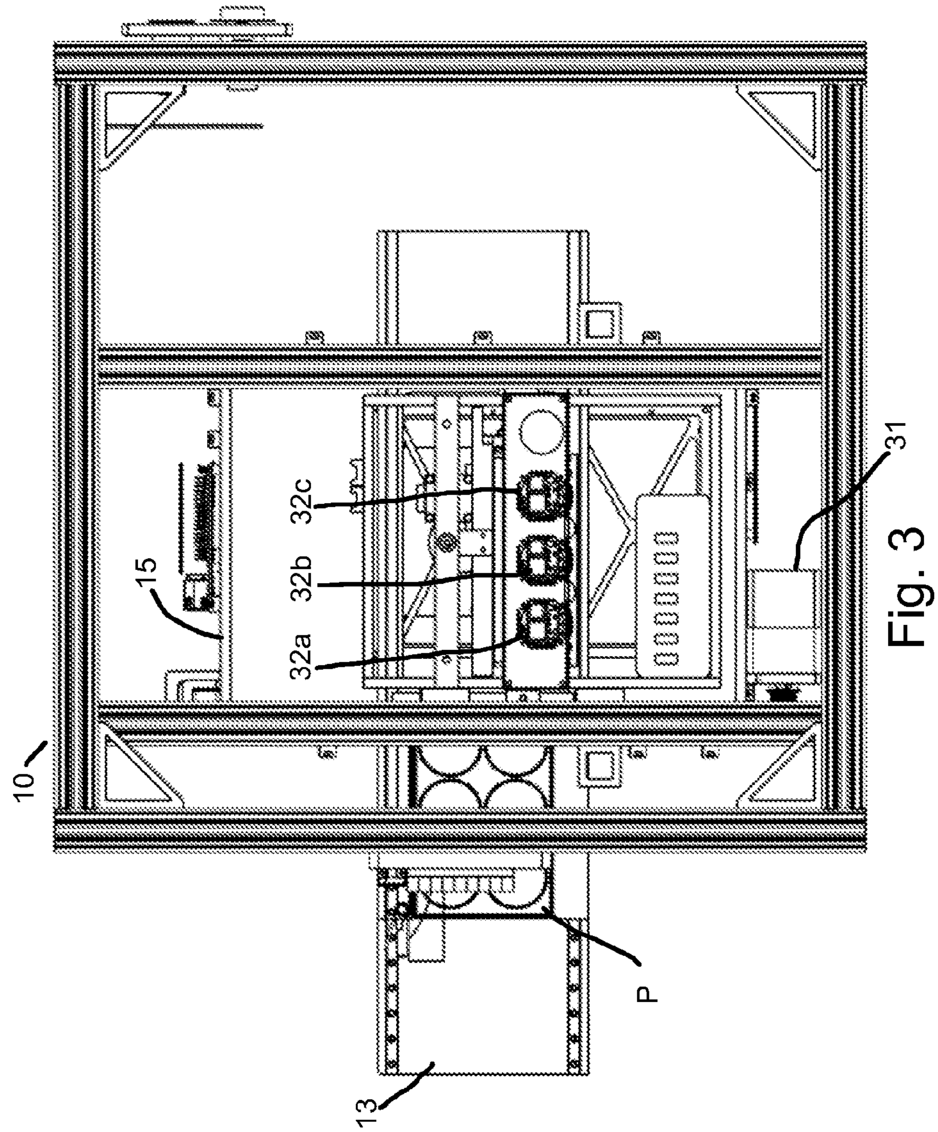
FIG. 3 is a top view of the imaging system of FIG. 1 with the walls removed.
Figure 4:
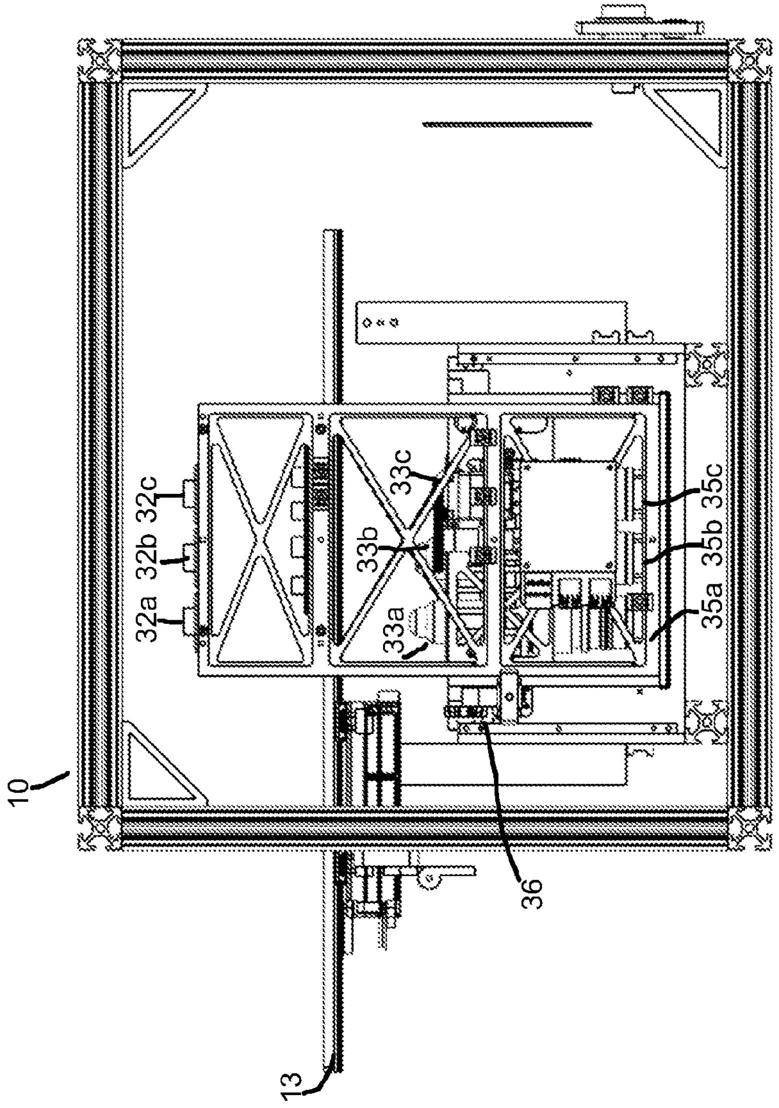
FIG. 4 is a right side view of the imaging system of FIG. 1.

FIG. 3 shows a top view of the imaging system where plate P having six wells is loaded for insertion into the system on platform 13. Motor 31 draws the platform 13 and the loaded plate P into the system 10. The motor 31 moves the platform 13 in both the X-direction into and out of the system and in the Y-direction by means of a mechanical transmission 36. The movement of the platform is to cause each of the wells to be placed under one of the LED light clusters 32*a*, 32*b*, and 32*c* which are aligned with microscope optics 33*a*, 33*b* and 33*c* respectively which are preferably 4×, 10× and 20× phase-contrast and brightfield optics which are shown in FIG. 4.

As used herein, an "imager" refers to an imaging device for measuring light (e.g., transmitted or scattered light), color, morphology, or other detectable parameters such as a number of elements or a combination thereof. An imager may also be referred to as an imaging device. In certain embodiments, an imager includes one or more lenses, fibers, cameras (e.g., a charge-coupled device or CMOS camera), apertures, mirrors, light sources (e.g., a laser or lamp), or other optical elements. An imager may be a microscope. In some embodiments, the imager is a bright-field microscope. In other embodiments, the imager is a holographic imager or microscope. In other embodiments, the imager is a fluorescence microscope.

As used herein, a "fluorescence microscope" refers to an imaging device which is able to detect light emitted from fluorescent markers present either within and/or on the surface of cells or other biological entities, said markers emitting light at a specific wavelength in response to the absorption a light of a different wavelength.

As used herein, a "bright-field microscope" is an imager that illuminates a sample and produces an image based on the light absorbed by the sample. Any appropriate bright-field microscope may be used in combination with an incubator provided herein.

As used herein, a "holographic imager" is an imager that provides information about an object (e.g., sample) by measuring both intensity and phase information of electromagnetic radiation (e.g., a wave front). For example, a holographic microscope measures both the light transmitted after passing through a sample as well as the interference pattern (e.g., phase information) obtained by combining the beam of light transmitted through the sample with a reference beam.

A holographic imager may also be a device that records, via one or more radiation detectors, the pattern of electromagnetic radiation, from a substantially coherent source, diffracted or scattered directly by the objects to be imaged, without interfering with a separate reference beam and with or without any refractive or reflective optical elements between the substantially coherent source and the radiation detector(s).

In some embodiments, an incubator cabinet includes a single imager. In some embodiments, an incubator cabinet includes two imagers. In some embodiments, the two imagers are the same type of imager (e.g., two holographic imagers or two bright-field microscopes). In some embodiments, the first imager is a bright-field microscope and the second imager is a holographic imager. In some embodiments, an incubator cabinet comprises more than 2 imagers. In some embodiments, cell culture incubators comprise three imagers. In some embodiments, cell culture incubators having 3 imagers comprise a holographic microscope, a bright-field microscope, and a fluorescence microscope.

As used herein, an "imaging location" is the location where an imager images one or more cells. For example, an imaging location may be disposed above a light source and/or in vertical alignment with one or more optical elements (e.g., lens, apertures, mirrors, objectives, and light collectors).

Figure 5:
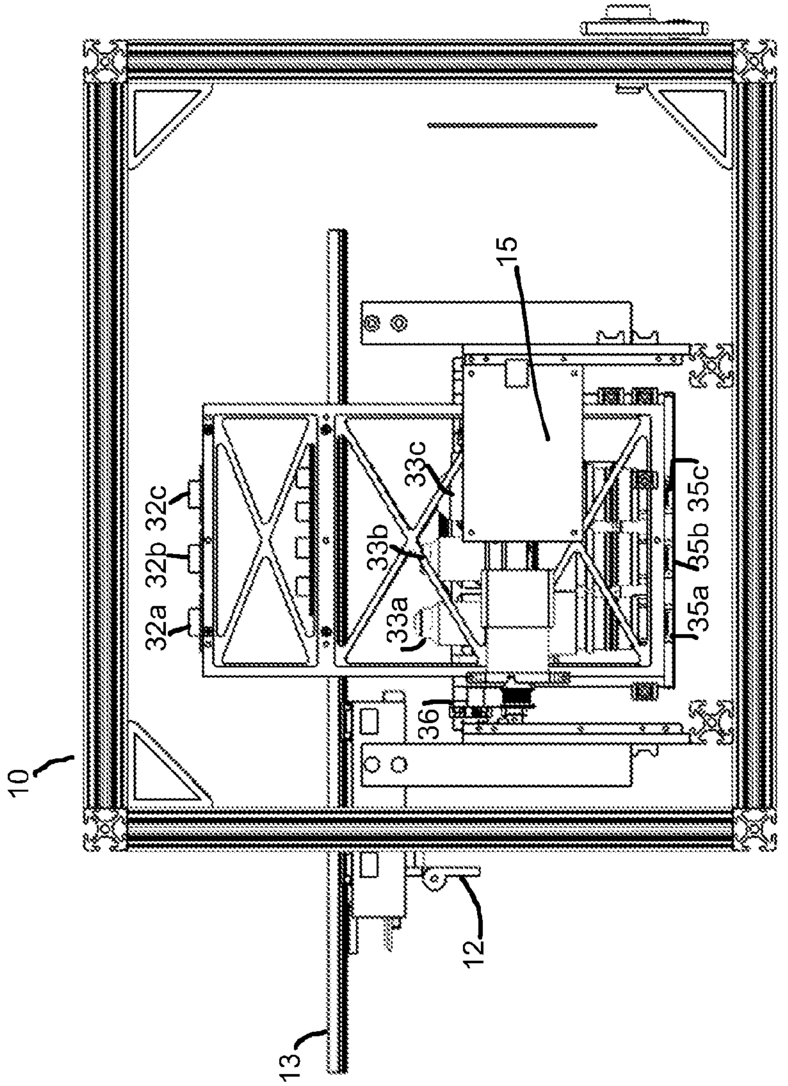
FIG. 5 is a left side view of the imaging system of FIG. 1.

Referring to FIGS. 4-5, Under the control of the circuitry on board 15, each well is aligned with a desired one of the three optical units 33*a*-33*c* and the corresponding LED is turned on for brightfield illumination. The image seen by the optical unit is recorded by the respective video camera 35*a*, 35*b*, and 35*c* corresponding to the optical unit. The imaging and the storing of the images are all under the control of the circuitry on board 15. After the imaging is completed, the platform with the loaded plate is ejected from the system and the plate can be removed and placed in an incubator. Focusing of the microscope optics is along the z axis and images taken at different distances along the z axis is called the z-stack.

Figure 6:
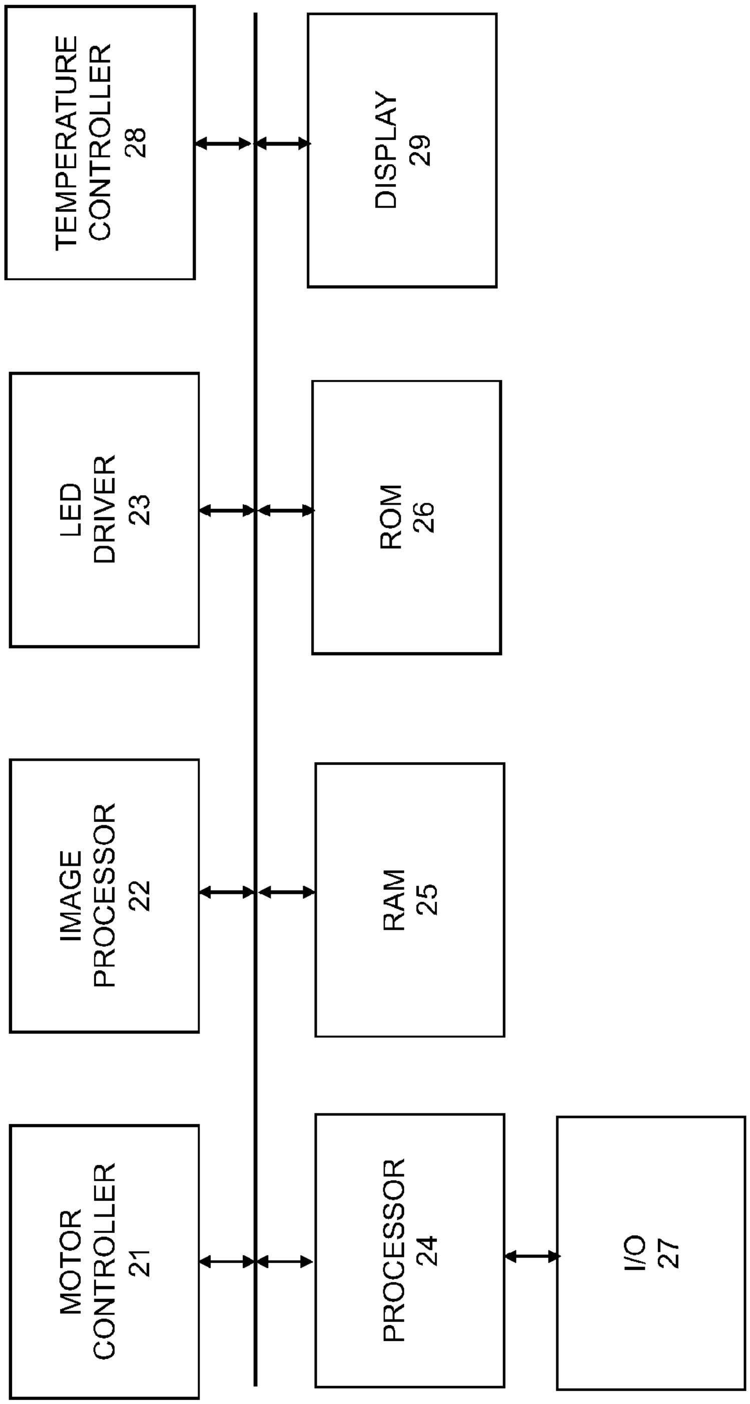
FIG. 6 is a block diagram of the circuitry of the imaging system of FIG. 1.

FIG. 6 is a block diagram of the circuitry for controlling the system 10. The system is run by processor 24 which is a microcontroller or microprocessor which has associated RAM 25 and ROM 26 for storage of firmware and data. The processor controls LED driver 23 which turns the LEDs on and off as required. The motor controller 21 moves the motor 15 to position the wells in an imaging position as desired by the user. In a preferred embodiment, the system can effect a quick scan of the plate in less than 1 minute and a full scan in less than 4 minutes.

The circuitry also includes a temperature controller 28 for maintaining the temperature at 98.6 degrees F. The processor 24 is connected to an I/O 27 that permits the system to be controlled by an external computer such as a laptop or desktop computer or a tablet such as an iPad or Android tablet. The connection to an external computer allows the display of the device to act as a user interface and for image processing to take place using a more powerful processor and for image storage to be done on a drive having more capacity. Alternatively, the system can include a display 29 such as a tablet mounted on one face of the system and an image processor 22 and the RAM 25 can be increased to permit the system to operate as a self-contained unit.

The image processing either on board or external, has algorithms for artificial intelligence and intelligent image analysis. The image processing permits trend analysis and forecasting, documentation and reporting, live/dead cell counts, confluence percentage and growth rates, cell distribution and morphology changes, and the percentage of differentiation.

When a new cell culture plate is imaged for the first time by the microscope optics, a single z-stack, over a large focal range, of phase contrast images is acquired from the center of each well using the 4× camera. The z-height of the best focused image is determined using the focusing method, described below. The best focus z-height for each well in that specific cell culture plate is stored in the plate database in RAM 25 or in a remote computer. When a future image scan of that plate is done using either the 4× or 10× camera, in either brightfield or phase contrast imaging mode, the z-stack of images collected for each well are centered at the best focus z-height stored in the plate database. When a future image scan of that plate is done using the 20× camera, a pre-scan of the center of each well using the 10× camera is performed and the best focus z-height is stored in the plate database to define the center of the z-stack for the 20× camera image acquisition.

Each whole well image is the result of the stitching together of a number of tiles. The number of tiles needed depend on the size of the well and the magnification of the camera objective. A single well in a 6-well plate is the stitched result of 35 tiles from the 4× camera, 234 tiles from the 10× camera, or 875 tiles from the 20× camera.

The higher magnification objective cameras have smaller optical depth, that is, the z-height range in which an object is in focus. To achieve good focus at higher magnification, a smaller z-offset needs to be used. As the magnification increases, the number of z-stack images needs to increase or the working focal range needs to decrease. If the number of z-stack images increase, more resources are required to acquire the image, time, memory, processing power. If the focal range decreases, the likelihood that the cell images will be out of focus is greater, due to instrument calibration accuracy, cell culture plate variation, well coatings, etc.

In one implementation, the starting z-height value is determined by a database value assigned stored remotely or in local RAM. The z-height is a function of the cell culture plate type and manufacturer and is the same for all instruments and all wells. Any variation in the instruments, well plates, or coatings needs to be accommodated by a large number of z-stacks to ensure that the cells are in the range of focus adjustment. In practice this results in large imaging times and is intolerance to variation, especially for higher magnification objective cameras with smaller depth of field. For example, the 4× objective camera takes 5 z-stack images with a z-offset of 50 μm for a focal range of 5*50=250 μm. The 10× objective camera takes 11 z-stack images with a z-offset of 20 μm for a focal range of 11*20=220 μm. The 20× objective camera takes 11 z-stack images with a z-offset of 10 μm for a focal range of 11*10=110 μm.

The processor 24 creates a new plate entry for each plate it scans. The user defines the plate type and manufacturer, the cell line, the well contents, and any additional experiment condition information. The user assigns a plate name and may choose to attach a barcode to the plate for easier future handling. When that plate is first scanned, a pre-scan is performed. For the pre-scan, the image processor 22 takes a z-stack of images of a single tile in the center of each well. The pre-scan uses the phase contrast imaging mode to find the best focus image z-height. The pre-scan takes a large z-stack range so it will find the focal height over a wider range of instrument, plate, and coating variation. The best focus z-height for each well is stored in the plate database such that future scans of that well will use that value as the center value for the z-height.

Although the pre-scan method was described using the center of a well as the portion where the optimal z-height is measured, it is understood that the method can be performed using other portions of the wells and that the portion measured can be different or the same for each well on a plate.

In one embodiment, the 4× pre-scan takes 11 z-height images with a z-offset of 50 μm for a focus range of 11*50=550 μm. For a 6-well plate, the 4× pre-scan takes 11 images per well, 6*11=66 images per plate. The 4× pre-scan best focus z-heights are used for the 4× and 10× scans. The additional imaging is not significant compared to the 35*5*6=1050 images for the 4× scan, and 234*11*6=15444 images for the 10× scan. For a 20× scan, the system performs a 10× pre-scan in addition to the 4× pre-scan to define the best focus z-height values to use as the 20× center z-height value for the z-stacks. It is advantageous to limit the number of pre-scan z-height measurements to avoid imaging the bottom plastic surface of the well since it may have debris that could confuse the algorithms.

In some embodiments, the pre-scan is most effective when performed in a particular imaging mode, such as phase contrast. In such a circumstance, the optimal z-height determined using the pre-scan in that imaging mode can be applied to other imaging modes, such as brightfield, fluorescence, or luminescence.

As noted, condensation buildup is a common problem encountered when imaging live cells, especially when moving the tissue culture plate from an incubator to a dry, cool area. Upon removal from the incubator, the temperature gradient between the base and the lid rapidly increases, with the lid cooling much faster than the media-containing base. This causes condensation to quickly build up on the lid. In addition, condensation can often be hard to see, especially when viewing in a bright room. Unless one uses oblique illumination with a flashlight (such as the flashlight on a smartphone), one will not be easily able to view condensation buildup.

When removing a 6-well tissue culture plate (containing 2 mL of media [DMEM-F12] or DPBS per well) from the incubator, in a room at 20° C. and 40% relative humidity, the lid begins to develop condensation within the first minute. Condensation buildup is known to negatively affect image quality, so having a mitigation strategy is important.

Figure 8:
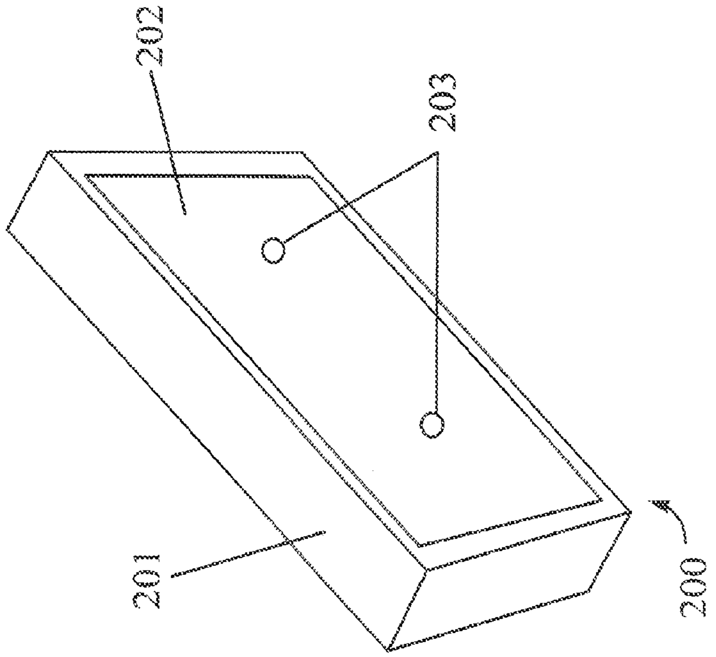
FIG. 8 shows a perspective view of a thermal block according to the present invention.

To ensure that condensation doesn't occur, we have developed thermal blocks to reduce the temperature gradient that forms in the plate once the plate leaves the incubator and is placed in the imager. The thermal block 200 shown in FIG. 8 has a metal side 202 and a plastic side 201 held together by screws 203. Before removing the plate 100 to be imaged from the incubator, place the thermal block 200 metal side 202 down, on top of the plate lid. The plate should be transported to the imager with the thermal block on top and should only be removed once the plate is ready to be inserted into the imager. Because the imager is typically set to 37° C., condensation should not occur. If light condensation does occur, it can be mitigated by leaving the plate in the imager for 5 minutes before imaging.

A key element of the condensation remediation device (thermal block) is that there is a high thermal conductivity layer which has been pre-heated in the incubator and is in close contact with the plate lid once it leaves the incubator.

In one embodiment, the high thermal conductivity layer is aluminum, but it could be another metal, or thermally doped plastic, or graphite, or ceramic, or a contained liquid.

In one embodiment, the high thermal conductivity layer is covered by a low thermal conductivity layer, which in this case is a plastic such as polyethylene. The low thermal conductivity layer allows the thermal block to be handled without being cooled by the contact, and it insulates the high thermal conductivity layer to make it stay hot longer. However, the remediation device would work without the low thermal conductivity layer, albeit less efficiently.

In one embodiment, the thermal block is designed for an SBS (Society for Biomolecular Screening) standard well plate so it has a rectangular cross-section of 5"×3.4". However, a thermal block designed for a petri dish would be round, a thermal block for a slide would be rectangular and 25 mm×75 mm, and all could be oversized with an arbitrary shape, or undersized for best fit on the lid.

In another embodiment, the idea of a temporary thermal block that heats the lid after it is removed from the incubator and then is removed before downstream measurements, is applied to cellular imaging, but it could also be used for any optical measurements whose performance will be negatively impacted by condensation.

The thermal block 200 is sized to the plate it is used within one embodiment, but can be oversized as well. The thickness of the metal layer is 0.125" to 1" and preferably 0.25" to 0.5". The thickness of the plastic layer in one embodiment is 0.0625" to 1", but preferably is 0.35". The claims are focused on our implementation.

In other embodiments the invention can be used with vessels other than cell culture plates, with optical instruments other than imagers and in embodiments where an upper lower thermal conductivity layer is not included.

The block is generally a rectangular solid shape although other shapes are within the scope of the invention. The edges can be rounded or sharp.

In accordance with the method of the present invention, the following method steps are performed:

a. Preheating the thermal block 200 in an incubator.
b. Upon retrieving the plate 100 to be imaged, the thermal block 200 should be placed metal side 202 down before or immediately after removing the plate from the incubator.
c. The tissue culture plate 100 should be carried to the imager with the thermal block 200 placed on the lid. Make sure to keep the thermal block placed on the tissue culture plate while setting up parameters on imager.
d. When ready to place the tissue culture plate 100 into the imager, eject the plate tray, remove the thermal block 200, insert the plate 100, and close the imager door.

The thermal block should be put back into the incubator as soon as possible, so it stays warm enough to be continually effective. If the thermal block is left out and cools to room temperature, it will have to re-equilibrate to 37° C. for maximum effectiveness. The thermal blocks can be disinfected with 70% ethanol.

If condensation under the lid persists, try leaving the plate in the imager for 5 minutes before imaging. If that proves ineffective, the lid may be swapped with a new lid that has been preheated in the incubator.

Figure 7:
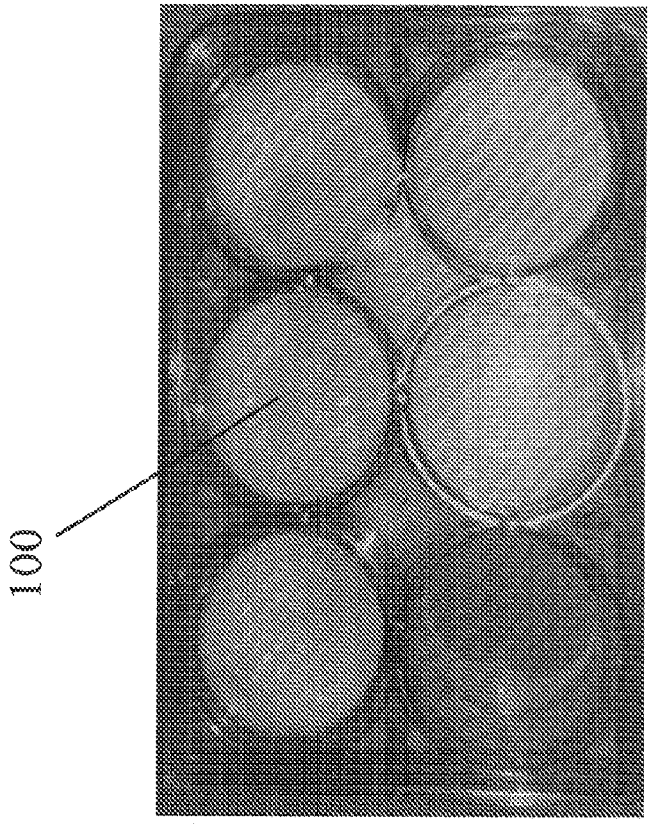
FIG. 7; shows a cell culture plate with condensation formed on it.

FIG. 7 shows a plate that was removed from the incubator and set on the bench for 180 seconds, allowing condensation to fully coat the lid over each well (one well left empty for visualization purposes). This plate is not ready for imaging.

Figure 10:
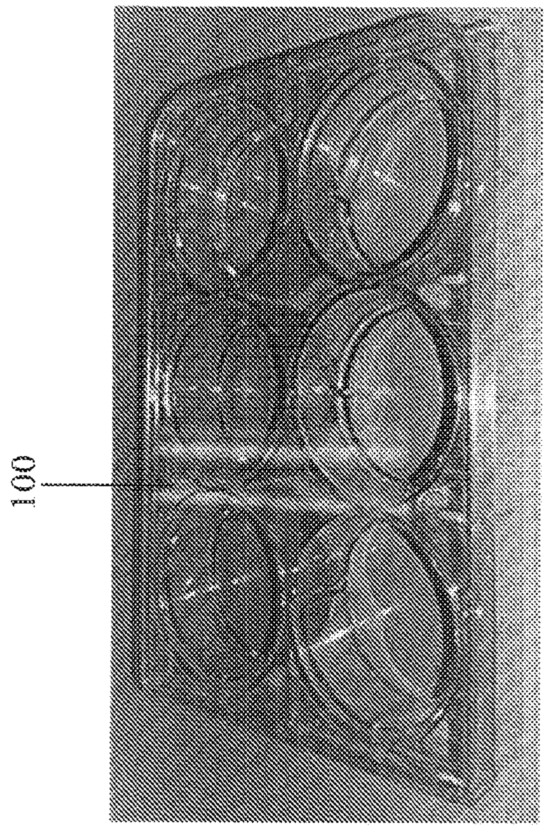
FIG. 10 shows a cell culture plate after having the thermal plate applied thereto.
Figure 9:
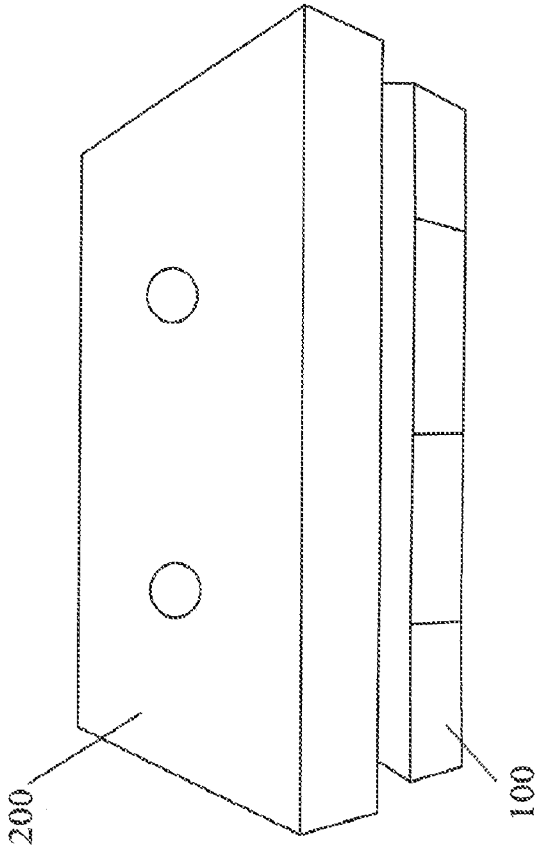
FIG. 9 shows the thermal block of FIG. 8 on a cell culture plate in accordance with the method of the present invention.

FIG. 10 shows the same plate after the thermal block was used for 180 seconds, clearing up all condensation on the lid. This plate is ready for imaging.

In other embodiments, the metal side can be a plate or an anodized layer. The metal is preferably aluminum, copper, iron or other metals having good thermal transmission properties. The plastic side can be polypropylene, polyethylene, acrylic or any thermal insulator.

In other embodiments, the visible screws are recessed. Additionally, a rim is added to the plastic side so that multiple plates can be stacked (similar to the rim that is molded into plate lids).

In addition, the aluminum metal plate can be anodized or coated to improve chemical resistance. Other metals or thermally loaded plastics can be used to create the thermal mass.

One or more imaging systems may be interconnected by one or more networks in any suitable form, including as a local area network (LAN) or a wide area network (WAN) such as an enterprise network or the Internet. Such networks may be based on any suitable technology and may operate according to any suitable protocol and may include wireless networks, wired networks, or fiber optic networks.

In another embodiment, the cell culture images for a particular culture are associated with other files related to the cell culture. For example, many cell incubators and have bar codes adhered thereto to provide a unique identification alphanumeric for the incubator. Similarly, media containers such as reagent bottles include bar codes to identify the substance and preferably the lot number. The files of image data, preferably stored as raw image data, but which can also be in a compressed jpeg format, can be stored in a database in memory along with the media identification, the unique incubator identification, a user identification, pictures of the media or other supplies used in the culturing, notes taken during culturing in the form of text, jpeg or pdf file formats.

In one embodiment, an app runs on a smartphone such as an IOS phone such as the iPhone 11 or an Android based phone such as the Samsung Galaxy S10 and is able to communicate with the imager by way of Bluetooth, Wi-Fi or other wireless protocols. The smartphone links to the imager and the bar code reader on the smartphone can read the bar code labels on the incubator, the media containers, the user id badge and other bar codes. The data from the bar codes is then stored in the database with the cell culture image files. In addition, the camera on the smartphone can be used to take pictures of the cell culture equipment and media and any events relative to the culturing to store with the cell culture image files. Notes can be taken on the smartphone and transferred to the imager either in text form or by way of scanning written notes into jpeg or pdf file formats.

The various methods or processes outlined herein may be coded as software that is executable on one or more processors that employ any one of a variety of operating systems or platforms. Such software may be written using any of a number of suitable programming languages and/or programming or scripting tools and may be compiled as executable machine language code or intermediate code that is executed on a framework or virtual machine.

One or more algorithms for controlling methods or processes provided herein may be embodied as a readable storage medium (or multiple readable media) (e.g., a non-volatile computer memory, one or more floppy discs, compact discs (CD), optical discs, digital versatile disks (DVD), magnetic tapes, flash memories, circuit configurations in Field Programmable Gate Arrays or other semiconductor devices, or other tangible storage medium) encoded with one or more programs that, when executed on one or more computing units or other processors, perform methods that implement the various methods or processes described herein.

In various embodiments, a computer readable storage medium may retain information for a sufficient time to provide computer-executable instructions in a non-transitory form. Such a computer readable storage medium or media can be transportable, such that the program or programs stored thereon can be loaded onto one or more different computing units or other processors to implement various aspects of the methods or processes described herein. As used herein, the term “computer-readable storage medium” encompasses only a computer-readable medium that can be considered to be a manufacture (e.g., article of manufacture) or a machine. Alternately or additionally, methods or processes described herein may be embodied as a computer readable medium other than a computer-readable storage medium, such as a propagating signal.

The terms “program” or “software” are used herein in a generic sense to refer to any type of code or set of executable instructions that can be employed to program a computing unit or other processor to implement various aspects of the methods or processes described herein. Additionally, it should be appreciated that according to one aspect of this embodiment, one or more programs that when executed perform a method or process described herein need not reside on a single computing unit or processor but may be distributed in a modular fashion amongst a number of different computing units or processors to implement various procedures or operations.

Executable instructions may be in many forms, such as program modules, executed by one or more computing units or other devices. Generally, program modules include routines, programs, objects, components, data structures, etc., that perform particular tasks or implement particular abstract data types. Typically, the functionality of the program modules may be organized as desired in various embodiments.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, e.g., elements that are conjunctively present in some cases and disjunctively present in other cases. Other elements may optionally be present other than the elements specifically identified by the “and/or” clause, whether related or unrelated to those elements specifically identified unless clearly indicated to the contrary. Thus, as a non-limiting example, a reference to “A and/or B,” when used in conjunction with open-ended language such as “comprising” can refer, in one embodiment, to A without B (optionally including elements other than B); in another embodiment, to B without A (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, e.g., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (e.g. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as “comprising,” “including,” “carrying,” “having,” “containing,” “involving,” “holding,” and the like are to be understood to be open-ended, e.g., to mean including but not limited to.

Only the transitional phrases “consisting of” and “consisting essentially of” shall be closed or semi-closed transitional phrases, respectively, as set forth in the United States Patent Office Manual of Patent Examining Procedures, Section 2111.03.

Use of ordinal terms such as “first,” “second,” “third,” etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for preventing condensation on a cell culture plate having wells to be imaged, comprising the steps of: preheating a block having a higher thermal conductivity layer configured to overlie all of the wells of the cell culture plate and an upper lower thermal conductivity layer above the higher thermal conductivity layer; removing the cell culture plate from an incubator; placing the preheated block on the cell culture plate, with the higher thermal conductivity layer resting on the plate, either before or immediately after removing the cell culture plate from the incubator; transporting the culture plate to an imager with the thermal preheated block in place; and removing the preheated block before or after inserting the culture plate into the imager.

2. The method according to claim 1, wherein the thermal block is removed before the cell culture plate is inserted in the imager.

3. The method according to claim 2, wherein the preheated block is placed on the cell culture plate immediately after removal from the incubator.

4. The method according to claim 1, wherein the higher thermal conductivity layer is a metal selected from aluminum, copper and iron.

5. The method according to claim 1, wherein the higher thermal conductivity layer is selected from metal, thermally doped plastic, graphite, ceramic, and a contained liquid.

6. The method according to claim 1, wherein the lower thermal conductivity layer is a plastic.

7. The method according to claim 1, wherein the lower thermal conductivity layer is selected from polypropylene, polyethylene, acrylic or any thermal insulator.

8. The method according to claim 1, wherein the block has a rectangular cross-section.

9. The method according to claim 1, wherein the block has a rim on the lower thermal conductivity side to permit stacking.

10. The method according to claim 1, wherein the preheated block is placed on the cell culture plate immediately after removal from the incubator.

* * * * *